(12) United States Patent
Reddy et al.

(10) Patent No.: US 12,004,818 B2
(45) Date of Patent: Jun. 11, 2024

(54) SYSTEM AND METHOD FOR PERFORMING AND EVALUATING A PROCEDURE

(71) Applicant: Medtronic Navigation, Inc., Louisville, CO (US)

(72) Inventors: Robert J. Reddy, Broomfield, CO (US); John B. Clayton, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 417 days.

(21) Appl. No.: 17/338,202

(22) Filed: Jun. 3, 2021

(65) Prior Publication Data
US 2021/0290318 A1    Sep. 23, 2021

Related U.S. Application Data

(62) Division of application No. 15/997,444, filed on Jun. 4, 2018, now Pat. No. 11,026,752.

(51) Int. Cl.
*A61B 34/20* (2016.01)
*A61B 34/10* (2016.01)
*A61F 2/44* (2006.01)

(52) U.S. Cl.
CPC .............. *A61B 34/20* (2016.02); *A61B 34/10* (2016.02); *A61B 2034/2051* (2016.02); *A61B 2034/2055* (2016.02); *A61B 2034/2063* (2016.02); *A61F 2/442* (2013.01); *A61F 2/4455* (2013.01)

(58) Field of Classification Search
CPC . A61B 34/20; A61B 34/10; A61B 2034/2051; A61F 2/442
See application file for complete search history.

(56) References Cited

U.S. PATENT DOCUMENTS

| | | | |
|---|---|---|---|
| 6,214,018 B1 | 4/2001 | Kreizman et al. | |
| 7,542,791 B2 * | 6/2009 | Mire | G16H 50/50 |
| | | | 600/407 |
| 7,660,623 B2 | 2/2010 | Hunter et al. | |
| 7,697,972 B2 | 4/2010 | Verard et al. | |
| 7,747,311 B2 | 6/2010 | Quaid, III | |
| 7,831,292 B2 | 11/2010 | Quaid et al. | |
| 7,899,512 B2 | 3/2011 | Labadie et al. | |
| 8,010,180 B2 * | 8/2011 | Quaid | A61B 34/71 |
| | | | 600/426 |

(Continued)

FOREIGN PATENT DOCUMENTS

EP    3289964 A1    3/2018

OTHER PUBLICATIONS

International Search Report and Written Opinion regarding International Application No. PCT/US2019/035218 dated Aug. 27, 2019.

(Continued)

*Primary Examiner* — Zade Coley
(74) *Attorney, Agent, or Firm* — Harness, Dickey & Pierce, P.L.C.

(57) ABSTRACT

Disclosed is a method and system for performing a procedure. The system may include a navigation system and/or a surgical robot to be used to at least assist in the procedure. The system may assist in delineating objects and/or determining physical characteristics of subject portions. The system may assist in performing and/or a workflow of the procedure.

6 Claims, 6 Drawing Sheets

(56) References Cited

U.S. PATENT DOCUMENTS

| | | | |
|---|---|---|---|
| RE44,305 E | 6/2013 | Foley et al. | |
| 8,560,047 B2 | 10/2013 | Haider et al. | |
| 8,644,907 B2 | 2/2014 | Hartmann et al. | |
| 8,717,430 B2 | 5/2014 | Simon et al. | |
| 8,842,893 B2 | 9/2014 | Teichman et al. | |
| 8,934,961 B2* | 1/2015 | Lakin | A61B 90/36 600/407 |
| 8,938,282 B2 | 1/2015 | Daon et al. | |
| 8,945,140 B2 | 2/2015 | Hubschman et al. | |
| 9,060,794 B2 | 6/2015 | Kang et al. | |
| 9,320,570 B2 | 4/2016 | Olson | |
| 9,345,552 B2 | 5/2016 | Janik et al. | |
| 9,452,024 B2 | 9/2016 | Daon et al. | |
| 9,788,906 B2* | 10/2017 | Piron | A61B 1/045 |
| 2004/0024311 A1* | 2/2004 | Quaid, III | A61B 90/36 600/428 |
| 2004/0199072 A1 | 10/2004 | Sprouse et al. | |
| 2008/0243142 A1* | 10/2008 | Gildenberg | G16H 30/40 606/130 |
| 2009/0024140 A1 | 1/2009 | Allen et al. | |
| 2009/0157059 A1 | 6/2009 | Allen et al. | |
| 2011/0118597 A1 | 5/2011 | Labadie et al. | |
| 2011/0257653 A1 | 10/2011 | Hughes et al. | |
| 2012/0109150 A1* | 5/2012 | Quaid | G06F 3/016 606/130 |
| 2012/0172795 A1* | 7/2012 | Sandhu | G16Z 99/00 604/95.01 |
| 2013/0053648 A1* | 2/2013 | Abovitz | A61B 90/30 600/249 |
| 2013/0060278 A1 | 3/2013 | Bozung et al. | |
| 2014/0228675 A1 | 8/2014 | Daon et al. | |
| 2014/0276943 A1 | 9/2014 | Bowling et al. | |
| 2015/0141801 A1* | 5/2015 | Jean | A61B 5/0066 606/107 |
| 2016/0074123 A1* | 3/2016 | Bly | A61B 34/20 600/424 |
| 2016/0242858 A1 | 8/2016 | Moctezuma de la Barrera et al. | |
| 2017/0007327 A1 | 1/2017 | Haider et al. | |
| 2018/0055575 A1 | 3/2018 | Krimsky | |

OTHER PUBLICATIONS

U.S. Appl. No. 15/997,444, U.S. Pat. No. 11,026,752, filed Jun. 4, 2018, Reddy, Robert J. et al.
Examination Report for related European Application No. 19731116.0; dated Aug. 9, 2023; 7 pages.
First Office Action for related CN Application No. 201980037919.9, Date of Disptach: Jan. 18, 2024; 23 pages.

* cited by examiner

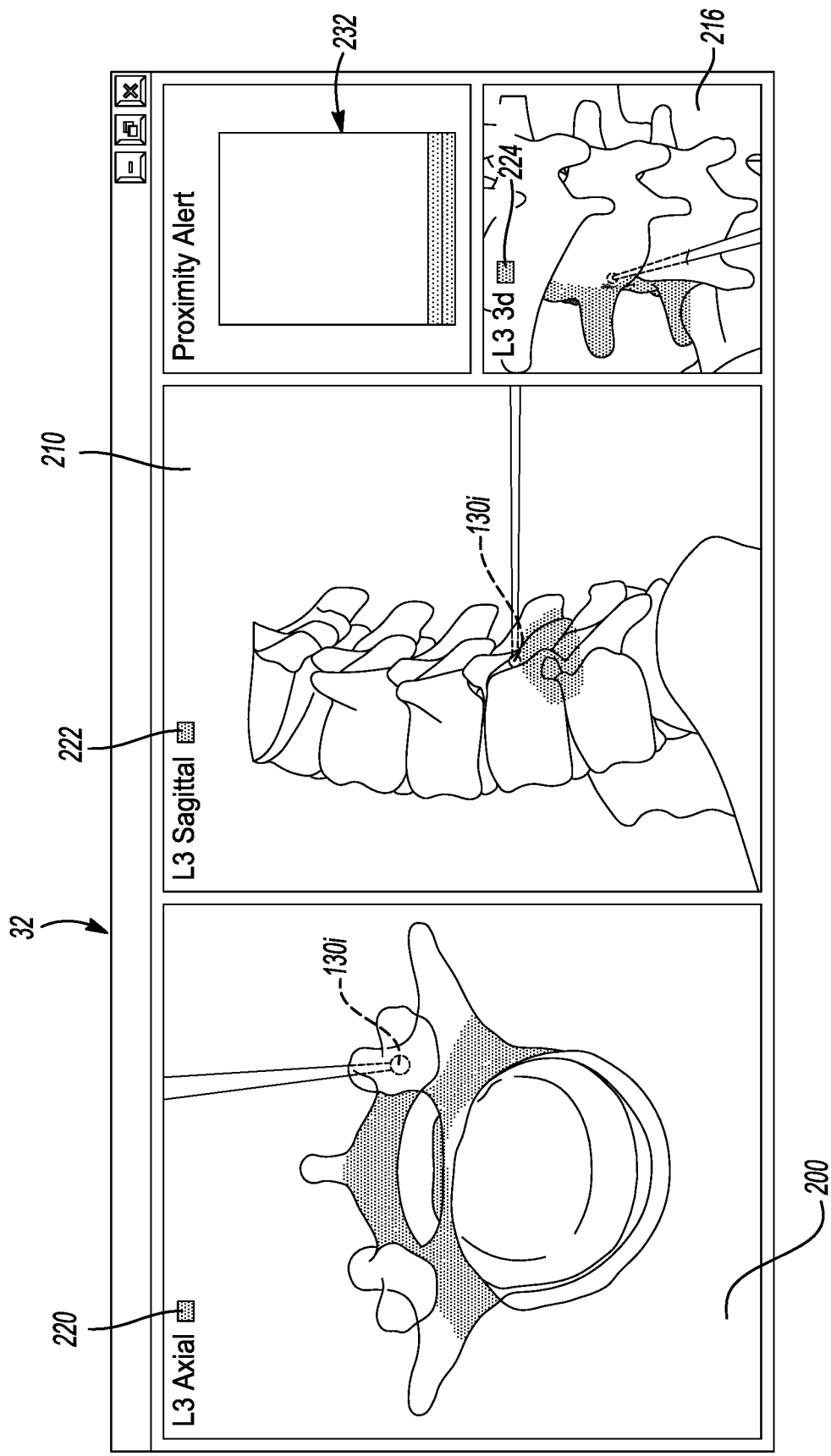

SYSTEM AND METHOD FOR PERFORMING AND EVALUATING A PROCEDURE

CROSS-REFERENCE TO RELATED APPLICATIONS

This application is a divisional of U.S. patent application Ser. No. 15/997,444 filed on Jun. 4, 2018. The entire disclosure of the above application is incorporated herein by reference.

FIELD

The subject disclosure relates generally to a system and method for determining a position, including location and orientation, of a member in space relative to a subject.

BACKGROUND

This section provides background information related to the present disclosure which is not necessarily prior art.

Various procedures may be selected to remove, repair or replace portions of a subject. For example, in a human subject a portion of the human anatomy may be selected to be removed, repaired or replaced. During the procedure, a minimally or low invasive procedure may be selected. The low invasive procedure may limit direct viewing of a work area within the subject, but may decrease recovery time and/or discomfort to the subject.

A navigation system for various procedures, such as surgical procedures, assembling procedures, and the like, allow an instrument or object to be tracked. Tracking systems may include appropriate tracking systems, such as optical, acoustic, electro-magnetic (EM), etc. EM tracking or navigation systems include the AxiEM™ electro-magnetic navigation system sold by Medtronic Navigation, Inc., having a place of business in Louisville, Colorado. The AxiEM™ electro-magnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument. Optical tracking systems include those such as the StealthStation® navigation system. The optical tracking system includes a set of cameras with a field of vision to triangulate a position of the instrument.

SUMMARY

This section provides a general summary of the disclosure, and is not a comprehensive disclosure of its full scope or all of its features.

A tracking device connected to an instrument is generally required to allow tracking and navigation of the instrument. The instrument, therefore, is generally specific to a tracking or navigation system. Disclosed is a system configured to determine the position of the tracked instrument and compare it to a predetermined volume or boundary. Generally, the tracked position may be used to indicate the relative position of the instrument to the predetermined areas and volume.

A system for performing a procedure is disclosed. The procedure may also be performed on a living subject such as an animal, human, or other selected patient. The procedure may include any appropriate type of procedure, such as one being performed on an inanimate object (e.g. an enclosed structure, airframe, chassis, etc.). Nevertheless, the procedure may be performed using a navigation system where a tracking system is able to track a selected one or more items.

A navigation system may be used to navigate an instrument relative to a subject during a selected portion of a procedure. In various embodiments, the procedure may include a procedure on a spine such as a decompression, spinal fusion (i.e. two or more vertebrae are connected together with a selected implant system or assembly) and/or discectomy. During a decompression a tissue, such as bone, removal instrument may be moved relative to a portion of the spine. The instrument may be tracked to allow a determination of the position of the instrument. The determined position may be illustrated along with or in the alternative to a relative position to predetermined volumes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is an illustration of a screen of a display device with a tracked instrument fourth position and indications, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
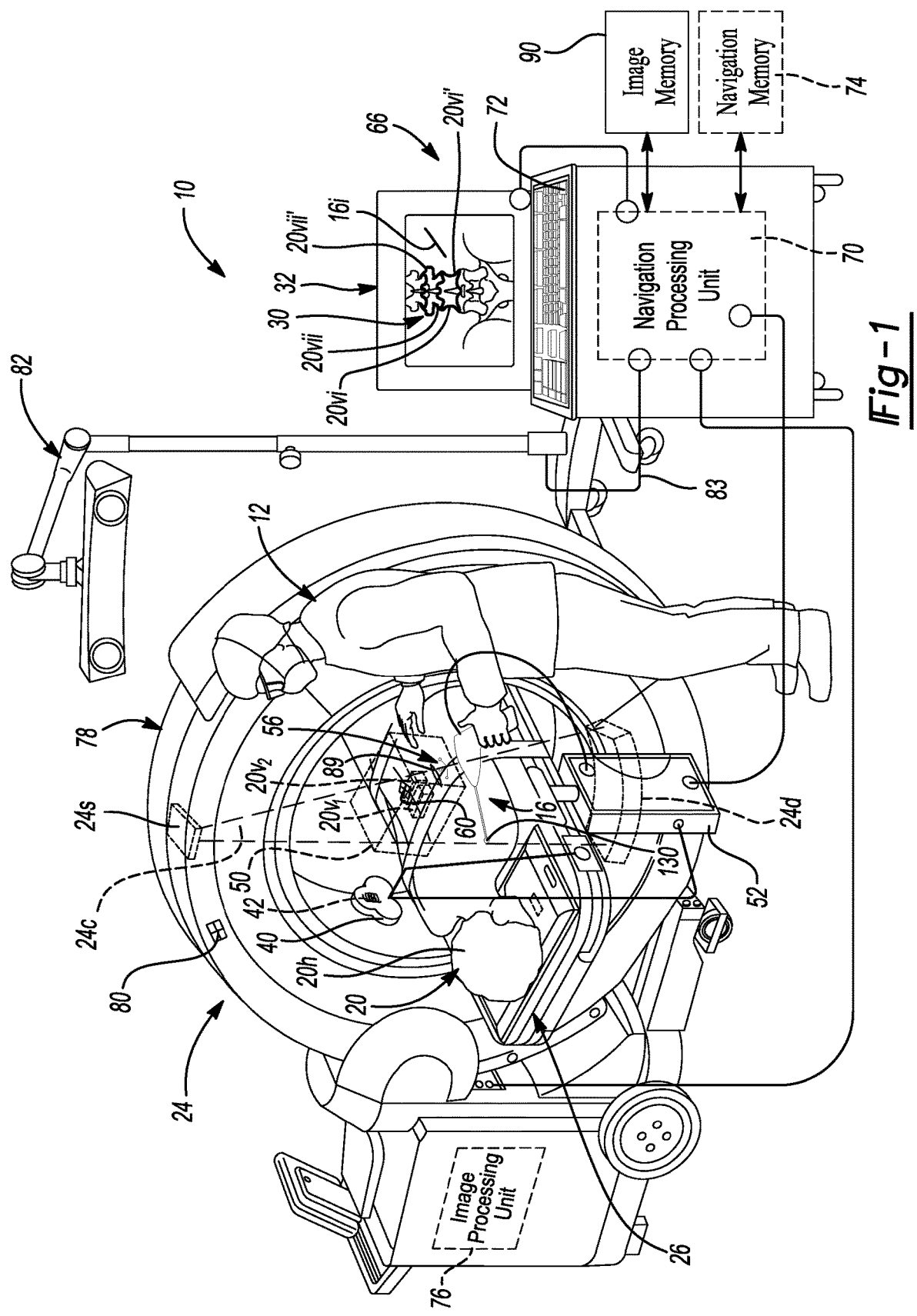
FIG. 1 is an environmental view of an operating suite including a navigation system, according to various embodiments.

With initial reference to FIG. 1, a navigation system 10 is illustrated. The navigation system 10 may be used for various purposes or procedures by one or more users, such as a user 12. The navigation system 10 may be used to determine or track a position of an instrument 16 in a volume. Exemplary instruments and systems includes those disclosed in U.S. Pat. No. 7,542,791, issued Jun. 2, 2009, incorporated herein by reference.

The position of the instrument may include both a three dimensional X,Y,Z location and orientation. Orientation may include one or more degree of freedom, such as three degrees of freedom. It is understood, however, that any appropriate degree of freedom position information, such as up to or less than six-degree of freedom position information, may be determined and/or presented to the user 12.

Tracking the position of the instrument 16 may assist the user 12 in determining a position of the instrument 16, even if the instrument 16 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20.

It is understood, however, that the instrument 16 may be tracked and/or navigated relative to any subject for any appropriate procedure. Tracking or navigating an instrument for a procedure, such as a surgical procedure, on a human or living subject is merely exemplary. The tracked instrument 16, tracked with a selected tracking system, as discussed herein, allows the position of the instrument to be determined. The determined position of the instrument 16 may also be compared to predetermined selected areas or volumes.

Figure 1A:
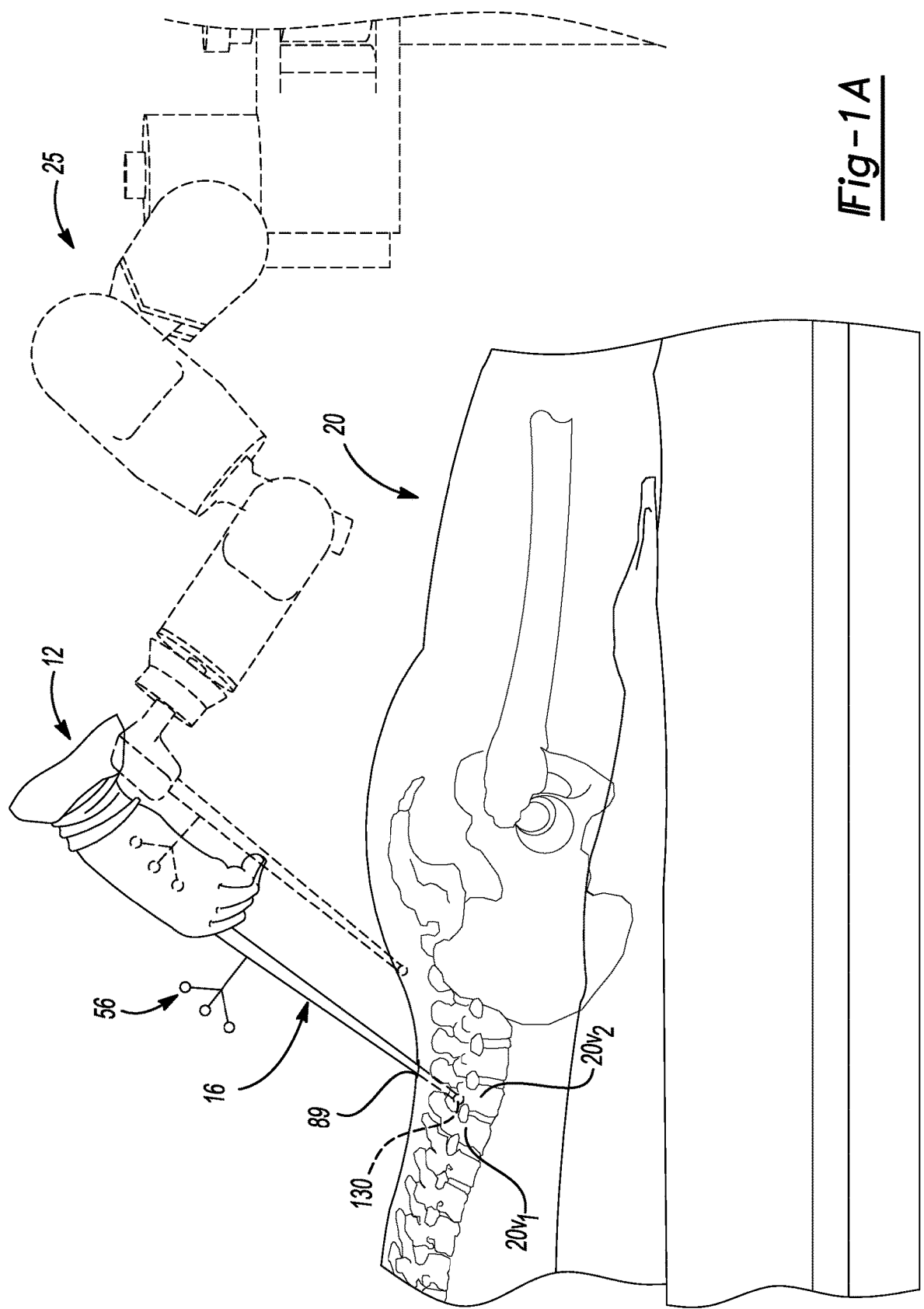
FIG. 1A is an environmental view of a user and a robotic system relative to a detailed portion of a subject, according to various embodiments.

Nevertheless, in various embodiments, the surgical navigation system 10, as discussed further herein, may incorporate various portions or systems, such as those disclosed in U.S. Pat. Nos. RE44,305; 7,697,972; 8,644,907; and 8,842,893; and U.S. Pat. App. Pub. No. 2004/0199072, all incorporated herein by reference. Various components that may be used with or as a component of the surgical navigation system 10 may include an imaging system 24 that is operable to image the subject 20, such as an O-Arm® imaging system, magnetic resonance imaging (MRI) system, computed tomography system, etc. A subject support 26 may be used to support or hold the subject 20 during imaging and/or during a procedure. The same or different supports may be used for different portions of a procedure. A surgical robotic system 25, as illustrated in FIG. 1A, may also be provided to assist in guiding or moving an instrument. Surgical robots include the Mazor X™ robotic guidance system sold by Medtronic, Inc. having place of business in Minnesota, USA.

In various embodiments, the imaging system 24 may include a source 24s. The source 24s may emit and/or generate X-rays. The X-rays may form a cone 24c, such as in a cone beam, that impinge on the subject 20. Some of the X-rays pass though and some are attenuated by the subject 20. The imaging system 24 may further include a detector 24d to detect the X-rays that are not completely attenuated, or blocked, by the subject 20. Thus, the image data may include X-ray image data. Further, the image data may be two-dimensional (2D) image data.

Image data may be acquired, such as with one or more of the imaging systems discussed above, during a surgical procedure or acquired prior to a surgical procedure for displaying an image 30 on a display device 32. In various embodiments, the acquired image data may also be used to form or reconstruct selected types of image data, such as three-dimensional volumes, even if the image data is 2D image data.

The trackable instrument 16 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 40, as illustrated in FIG. 1. In various embodiments, it is understood by one skilled in the art, that other appropriate tracking systems may be used including optical, radar, ultrasonic, etc. For example, an optical localizer 82 may be used to track the instrument 16.

The discussion herein of the EM localizer 40 and tracking system is merely exemplary of tracking systems operable with the navigation system 10. The position of the instrument 16 may be tracked in the tracking volume relative to the subject 20. The position, or selected portion of the instrument 16, may then be illustrated as a graphical representation, also referred to as an icon, 16i with the display device 32. In various embodiments, the icon 16i may be superimposed on the image 30 and/or adjacent to the image 30. As discussed herein, the navigation system 10 may incorporate the display device 32 and operate to render the image 30 from selected image data, display the image 30, determine the position of the instrument 16, determine the position of the icon 16i, etc.

With reference to FIG. 1, the EM localizer 40 is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form a navigation domain or volume 50, such as encompassing all or a portion of a head 20h, spinal vertebrae 20v, or other appropriate portion. The coils may be powered through a TCA controller and/or power supply 52. It is understood, however, that more than one of the EM localizers 40 may be provided and each may be placed at different and selected locations.

The navigation domain or volume 50 generally defines a navigation space or patient space. As is generally understood in the art, the instrument 16, such as a probe, may be tracked in the navigation space that is defined by a navigation domain relative to a patient or subject 20 with an instrument tracking device 56. For example, the instrument 16 may be freely moveable, such as by the user 12 or by and/or with a surgical robot, relative to a dynamic reference frame (DRF) or patient reference frame tracker 60 that is fixed relative to the subject 20. Both the tracking devices 56, 60 may include tracking portions that are tracked with appropriate tracking systems, such as sensing coils (e.g. conductive material formed or placed in a coil) that senses and are used to measure a magnetic field strength, optical reflectors, ultrasonic emitters, etc. Due to the tracking device 56 connected or associated with the instrument 16, relative to the DRF 60, the navigation system 10 may be used to determine the position of the instrument 16 relative to the DRF 60.

The navigation volume or patient space may be registered to an image space defined by the image 30 of the subject 20 and the icon 16i representing the instrument 16 may be illustrated at a navigated (e.g. determined) and tracked position with the display device 32, such as superimposed on the image 30. Registration of the patient space to the image space and determining a position of a tracking device, such as with the tracking device 56, relative to a DRF, such as the DRF 60, may be performed as generally known in the art, including as disclosed in U.S. Pat. Nos. RE44,305; 7,697,972; 8,644,907; and 8,842,893; and U.S. Pat. App. Pub. No. 2004/0199072, all incorporated herein by reference.

The navigation system 10 may further include and or be in communication with a navigation processor system 66. The navigation processor system 66 may include connections to the display device 32, the TCA 40, the TCA controller 52, and other portions and/or connections thereto. For example, a wire connection may be provided between the TCA controller 52 and a navigation processing unit 70. It is understood that the navigation processing unit 70 may include one or more processors of various types (e.g. general purpose processors executing accessed instructions and/or specific processors (e.g. ASIC)). Further, the navigation processor system 66 may have one or more user control inputs, such as a keyboard 72 (or others including a touch capacitive display, pen input, mouse, etc.), and/or have additional inputs such as from communication with one or more memory systems 74, either integrated or via a communication system. The navigation processor system 66 may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, CO.

Tracking information, including information regarding the magnetic fields sensed with the tracking devices 56, 60, may be delivered via a communication system, such as the TCA controller, which also may be a tracking device controller 52, to the navigation processor system 66 including the navigation processor 70. Thus, the tracked position of the instrument 16 may be illustrated as the icon 16i relative to the image 30. Various other memory and processing systems may also be provided with and/or in communication with the processor system 66, including the memory system 72 that is in communication with the navigation processor 70 and/or an imaging processing unit 76.

The image processing unit 76 may be incorporated into the imaging system 24, such as the O-Arm® imaging system, as discussed above. The imaging system 24 may, therefore, including the various portions such as a source and a x-ray detector that are moveable within a gantry 78. The imaging system 24 may also be tracked with a tracking device 80. It is understood, however, that the imaging system 24 need not be present while tracking the tracking devices, including the instrument tracking device 56. Also, the imaging system 24 may be any appropriate imaging system including a MRI, CT, etc.

In various embodiments, the tracking system may include an optical localizer 82. The optical localizer 82 may include one or more cameras that view or have a field of view that defines or encompasses the navigation volume 50. The optical localizer 82 may receive light (e.g. infrared or ultraviolet) input to determine a position or track the tracking device, such as the instrument tracking device 56. For example, at least two cameras at a fixed position relative to one another may view both the tracking device 56 of the instrument 16 and the DRF 60 on the patient 20. Due to registration, the tracking system and the navigation system 10 may then determine the position of the instrument 16 (including at least a portion thereof) relative to the subject 20. Generally, the position may be triangulated using the view of the volume 50. It is understood that the optical localizer 82 may be used in conjunction with and/or alternatively to the EM localizer 40 for tracking the instrument 16 and also may have a communication line 83 with the navigation processor system 66.

Information from all of the tracking devices may be communicated to the navigation processor 70 for determining a position of the tracked portions relative to each other and/or for localizing the instrument 16 relative to the image 30. The processor 70 may execute instructions or be designed to analyze the incoming navigation signals to determine the position of the instrument 16, as is generally understood in the art as discussed above. The determined position of the instrument 16, however, may be displayed with the display device 32 in various manners and with various indications, as discussed herein. The imaging system 24 may be used to acquire image data to generate or produce the image 30 of the subject 20. It is understood, however, that other appropriate imaging systems may also be used. The TCA controller 52 may be used to operate and power the EM localizer 40, as discussed above.

The image 30 that is displayed with the display device 32 may be based upon image data that is acquired of the subject 20 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-Arm® imaging system. The 2D image data may then be used to reconstruct a 3D image or model of the imaged subject, such as the patient 20. The reconstructed 3D image and/or an image based on the 2D image data may be displayed. Thus, it is understood by one skilled in the art that the image 30 may be generated using the selected image data.

Further, the icon 16i, determined as a tracked position of the instrument 16, may be displayed on the display device 32 relative to the image 30. In addition, the image 30 may be segmented, for various purposes, including those discussed further herein. Segmentation of the image 30 may be used to determine and/or delineate objects or portions in the image. In various embodiments, the delineation may be used to identify boundaries of various portions within the image 30, such as boundaries of one or more structures of the patient that is imaged, such as the vertebrae 20v. Accordingly, the image 30 may include an image of one or more of the vertebrae 20v, such as a first vertebra 20vi and a second vertebra 20vii. In various embodiments, the delineation may be represented, such as with selected icons, such as an icon 20vi' or a second icon 20vii'. The boundaries 20vi', 20vii' may be determined in an appropriate manner and for various purposes, as also discussed further herein. Selected anatomical portions may include displaying a disc between vertebrae and or determining that a disc is between determined vertebrae. For example, in various imaging modalities, soft tissue of a disc may not be easily or directly viewable, while the bone of the vertebrae is easily viewed by the user 12.

With continuing reference to FIG. 1, the subject 20 may include a plurality of vertebrae, such as a first vertebra $20v_1$ and a second vertebra $20v_2$. The vertebrae 20v may be surrounded or covered by soft tissue, such as a dermis, muscle, nerves, spinal cord and the like. In performing selected procedures, such as in a spinal fusion, discectomy, or other procedures, a small incision 89 may be made. A small incision may allow for a substantially minimal or low invasive procedure. For example, the incision may generally be about 1 millimeter (mm) to about 3 centimeters (cm) in length. Generally the incision allows access for instruments, such as the instrument 16 to a selected area while minimizing the incision size, which may also limit the view of the user 12 of the area where a procedure is occurring. In various procedures, such as in a spinal fusion, spinal decompression, or the like, material may be removed or impinged with the instrument 16. For example, portions of one or more vertebrae may be removed, such as the vertebrae $20v_1$ and $20v_2$. The two vertebrae may be any appropriate vertebrae, such as a third lumbar vertebra ($L_3$) and a fourth lumbar vertebra ($L_4$).

As illustrated in FIG. 1, the image 30 may include the vertebrae of the subject, along with other tissue of the subject 20. As discussed further herein, an illustration of the vertebrae may include the image acquired with the imaging system 24, or any appropriate imaging system, or a selected reconstruction thereof, such as a three-dimensional reconstruction.

In various embodiments, the imaging system 24, or any appropriate imaging system, may include an image processing unit 76 that may be used to analyze and allow for manipulation of selected images. The images may be stored with the imaging system 24 and/or stored in a selected image memory 90. Further, various instructions such as tracking, registration, and the like may be stored in the navigation memory 74.

With continuing reference to FIG. 1, during a selected procedure, such as a decompression, bone spur removal, tumor removal, or the like, a procedure may occur to remove a selected portion of the subject 20. It may be selected, during the procedure, to attempt or ensure minimizing or eliminating contact of a selected instrument, such as the navigated instrument 16, relative to selected areas of the subject 20. In various embodiments, a decompression or tumor removal may occur relative to one or more of the vertebrae $20v_1$ or $20v_2$. It is understood, however, that the vertebrae $20v$ are generally near nerve tissues and nerve bundles, such as the spinal cord and nerve roots or bundles that extend from the spinal cord to various portions of the subject 20. It may be selected, such as by the user 12, to attempt to eliminate contact or movement of the instrument into the nerve tissues.

Figure 2:
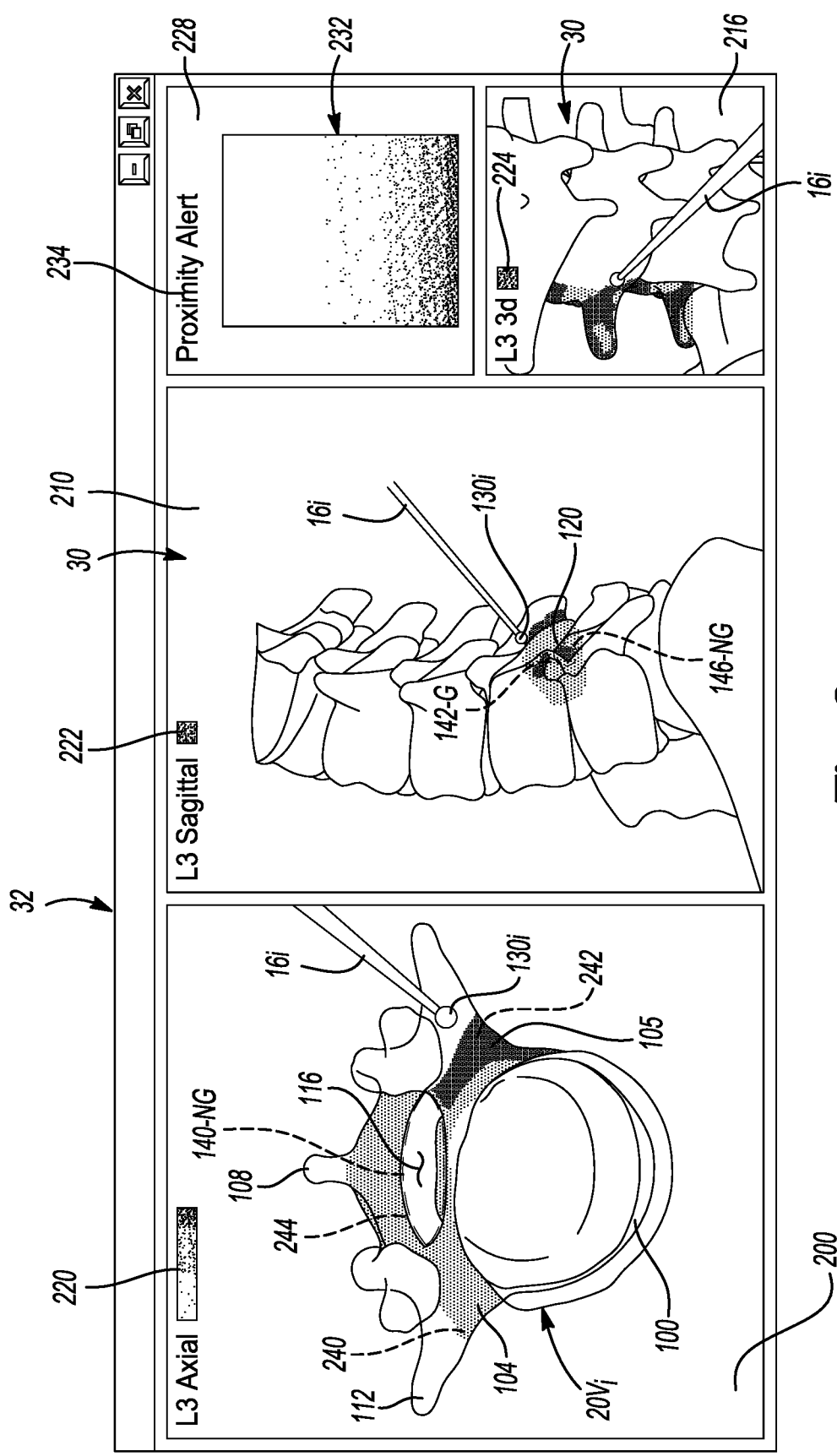
FIG. 2 is an illustration of a screen of a display device with a tracked instrument first position and indications, according to various embodiments.

For example, with additional reference to FIG. 2, the vertebra $20v_1$ may be included in the image 30 as imaged vertebra $20vi$. The vertebra $20v$ may include various anatomical features such as a vertebral body 100, a first pedicle 104, a second pedicle 105, a spinous process 108, a facet joint, the lamina, and transverse processes 112. The vertebra $20vi$, including the various anatomical portions, as discussed above, may surround or define a vertebral foramen 116. Within the vertebral foramen 116 the spinal cord (not specifically illustrated) may be positioned. The spinal cord may extend from near the head $20h$ of the subject 20 through the vertebral foramen 116 of all of the vertebrae to various portions of the anatomy. Nerve bundles or roots may extend from the spinal cord near the pedicles 104, 105. Accordingly, impingement or boney growths near the pedicles 104, 105 and/or the body 100 may extend into the nerve bundle or root regions 120. Removal of the bony growths, such as bone spurs or tumors, may be selected to relief pressure on the nerve bundles.

During a selected procedure, the user 12 and/or the surgical robot may move the instrument 16 to perform the bone removal procedure. In various embodiments, the instrument 16 may include a working end 130 (FIG. 1). The working end 130 may include any appropriate working end such as a burr, grater, cutter, or the like. The working end 130 may be positioned relative to selected portions of the anatomy, such as a bone spur or tumor, to remove the selected portion of the anatomy. In the decompression procedure, therefore, pressure may be removed from the nerve bundle, including the spinal cord, to increase a volume or are of the spinal canal 116 or the area near the pedicle 104 where the nerve bundles exit.

The instrument 16 may be tracked with the tracking device 56 with an appropriate tracking system, including the optical localizer 82 and/or the EM localizer 40. A known geometry of the instrument 16 allows the determination of the position of the working end 130 relative to the tracking device 56 even when the tracking device is not fixed at the distal end 130, as is understood in the art as discussed above. It is understood, however, that any appropriate navigation system be used to track the location of the instrument 16 with the tracking device 56. In various embodiments, the tracking device 56 may include one or more elements (e.g. spheres) that are viewable by the cameras of the optical localizer 82. Therefore the user 12 may move the instrument 16, including the working end 130, while it is tracked with the navigation system 10. As discussed above the patient 20 may be registered to the images 30 such that a position of the tracked instrument 16 may be illustrated relative to the images 30, such as with the icon 16i. Further, specific portions of the instrument may also be tracked, such as the working end 130, and may also be illustrated with appropriate icons such as a working end icon 130i.

The user 12 may also specifically define selected areas relative to the anatomy, such as the vertebrae $20v_1$ and $20v_2$ and the nerve bundles in the spinal canal 116. The predefined areas may be defined relative to the vertebrae $20v$ using the images 30 or other appropriate defining or identifying regions or methods.

With continuing reference to FIG. 1 and FIG. 2, the user 12 may view the image 30 at any appropriate time, such as immediately prior to a surgical procedure, or other appropriate procedure, during a planning phase. The planning phase may be any time prior to placing the instrument within the subject 20, such as hours or days before a procedure, or at any appropriate time. Nevertheless, during the planning phase, the user 12 may define working areas or planned working areas and nonworking or non-planned working areas. In defining the areas, the user 12 may view the images 30 or any appropriate portion to define the selected areas. For example, as illustrated in FIG. 2, the user may define an area within the vertebral foramen 116 as a no-go or a no-planned go area 140. The user 12 may also define areas near the pedicles 104, 105 as planned go areas 142. As understood by one skilled in the art, however, the pedicles 104, 105 may be near where nerve bundles exit the vertebral foramen 116 through an opening near or adjacent to the pedicles 104, 105. Accordingly the user 12 may define a second or additional no-go or no-planned go area 146. The user 12 may further define other areas within the image 30 as go or no-go areas. Each of the areas or volumes 140, 142, 146 may be defined with a discrete edge or boundary.

The user may define the areas using selected inputs 72, including a keyboard, mouse, or finger or the like. Additionally, computer algorithms may define the selected area. For example, the display device 32 may accept touch input such as with a capacitive display and/or selected input pen. The user 12 may trace areas or volumes and define the areas or volumes as go or no-go areas for a selected procedure. As the images 30 are registered to the patient or subject 20 during a selected procedure, the defined areas 140, 142, 146, may then be determined in the subject space of the subject 20. When tracking the instrument 16, the navigation system 10 may then determine whether the instrument 16, or at least a portion thereof such as the working end 130, is in one of the predetermined areas or volumes 140, 142, 146. Accordingly, the navigation processing unit 70 may access the images, which may be stored, compare them to a tracked location of the instrument 16, including the working end 130, as discussed further herein.

The user 12 may also define a selected distance from the defined boundary or volumes 140, 142, 146. For example, an approach area or distance may include increments of 0.1 mm to about 1 mm. For example the boundary 140 of the vertebral foramen 116 may be defined by the user 12. Also defined by the user, and/or defined by the navigation system 10, may be an approach distance or boundary relative to the defined area 140. The approach distance may be used to determine a notice or indication to the user 12 as the instrument 16 moves toward the defined area 140, but yet has not engaged or impinged upon the area 140. Accordingly, the gradation or incremental distance measurements may be any appropriate increment such as 0.1 mm, 0.2 mm, 0.5 mm, or the like. Further a maximum distance from the area 140 may be defined as a no-notice or safe area separate from the planned go area 142. For example, a maximum distance of 0.5 cm to about 1.5 cm may be determined by the user 12 and/or predetermined by the navigation system 10. Thus, as discussed further herein, when the instrument 16 is tracked and the position of the instrument 16 is determined to be outside of the minimum distance (e.g. at least 1 cm) away from the area 140, including a boundary defining the area 140, no indication may be provided to the user of a proximity or close proximity of the instrument 16 to the no-go area 140. Once the instrument passes the minimum distance or fence, however, the user 12 may be given an indication of proximity of the instrument 16 to the predetermined area.

With continuing reference to FIGS. 1 and 2, the user 12 may perform a procedure after determining the selected areas or volumes, such as the no-go areas or volumes 140, 146 and the planned go area or volume 142. Each of the volumes 140, 142, 146 may include boundaries or borders defined by the user 12 or computer algorithm. The user 12 and/or surgical robot may then use the tracked instrument 16, including the working end 130, to move the working end 130 toward the planned go area 142. As the instrument 16 moves toward the area of the subject 20, such as near the vertebrae 20v, indications may be made on the display device 32.

Indications may include various indications on one of more views. Generally, the indications may include visually perceptible indications displayed with the display device 32. The indications may be displayed relative to and/or directly on the image 30. The indications provide a visual indication to the user 12 of the relative tracked position of the instrument 16 and/or the working end 130. The indications may be visual representations of color, size, opacity, gradient, etc.

For example, as illustrated in FIG. 2, the display device 32 may include the images 30 in a plurality of windowed views. For example, an axial view 200 may be displayed of the image 30, a sagittal view 210 of the image 30 may be displayed, and a 3D model in a window 216 may be displayed of the image 30. Each of the displays 200, 210, 216 may display a selected view of the image 30 for reference by the user 12. Each of the views may include indications relative thereto. As discussed herein, the indication may be directly on the image and/or placed a distance from the image 30. The indication is regarding the tracked position of the instrument 16 relative to one or more of the predefined areas 140-146.

Indications may include an indication bar or portion 220, 222, or 224 in the respective view windows 200, 210, 216. The bars may be positioned in the respective windows in any appropriate manner, such as to grow horizontally and/or change in a visual manner (e.g. color, opacity, gradient, etc.) relative to the display windows. As discussed further herein, therefore, the indications 220, 222, 224 may increase in size, change color, and the like depending upon the tracked position of the instrument 16. Further, a separate window 228 may be positioned on the display device 32 relative to one or more of the other windows to provide an overall indication 232 and may include a label such as proximity alert or proximity indication 234. The indicator 232 of the proximity indication window 228 may include a maximum or closest indication of any of the indicators to one or more of the no-go areas 140, 146. Accordingly, each of the individual windows including the indicators 220, 222, 224, may include indication regarding a position of the instrument 16 relative to the defined areas in each of the respective views while the proximity indication 232 may provide an overall closest indication which may vary amongst the different views given the three-dimensional nature of the vertebrae 20v and the subject 20. Additionally, audible indications may be used relative to the pre-defined boundaries or borders.

With continuing reference to FIG. 2, the indications may further include indications at or directly on the image 30. For example, as illustrated in FIG. 2, near the pedicles 104, 105 and near the spinous process 108 around the areas defined by the user 140, 142, 146, the image 30 may appear to be color coded or otherwise visually distinguishable from surrounding areas. For example, the indicators 220 may be augmented or alternatively provided as color coding portions of the image 30. Accordingly, the image 30 may include an indication coloring or marking 240 near the pedicle 140, a coloring or indication 242 near or at the pedicle 105, and a coloring or indication 244 near or at the spinous process 108. Each of the direct indications 240, 242, 244, may change (e.g. change color, change darkness, change visual indication, change audible alert, etc.) based upon a tracked position of the instrument 16 relative to the defined areas 140, 142, 146. For example, similar to the indications 220, 222, 224, 232, the direct image indications 240, 242, 244 may darken or change color from a first color, such as yellow, to a darker or second color, such as red, as the instrument moves toward the no-go area 146 in the respective views. When audible indications are given, the type, frequency, volume, etc. of audible indication may also change rather than and/or in addition to a color change.

The robot 25 may also be provided to give the indication, rather than the visual indicator, noted above, the indication may be feedback (e.g. haptic feedback or force feedback) to the user 12 and or limit placement or movement with the robot 25 itself. The robot 25, for example, may be moved by the user 12 with the instrument within a manipulator and/or guide portion of the robot 25. The robot 25 may, therefore, may be used to provide the indication to the user such as with haptic feedback to the user 12 as the robot 25 is moved to move the instrument 16 relative to the define areas or volumes, as discussed above. The type or intensity of the haptic feedback may change. Further, the robot 25 may be configured and operated to limit movement (e.g. stop movement) of the instrument 16 relative to the defined areas or volumes 140, 142, 146.

As illustrated in FIG. 2, however, when the instrument 16 is near only a selected portion, such as the pedicle 105, only that portion of the indication 242 may alter or change appearance due to the tracked position of the instrument 16. Accordingly, the indications 240, 244, may remain substantially unchanged and only identify those regions that are generally being monitored for the possible location of the instrument 16, including the working end 130, relative to the image 30. It is further understood that the user 12 and/or the navigation system 10 automatically determines a selected portion of the instrument 16 to be tracked or identified with the indications. For example, the user 12 may identify the working end 130 as the relevant portion of the instrument 16 to be indicated with the indicators while a shaft connected to the working end 130 may be less critical or identified as not being relevant to the indications for providing to the user.

As discussed further herein, the various indications may be altered in visual appearance, such as color or color density, to provide indication to the user 12 of a tracked position of the working end 130 relative to selected predefined areas or volumes, such as the no-go volume 146. As discussed above, as the working end 130 moves toward or past a boundary, such as 1 cm away from the defined no-go volume 146, the indicators may appear and begin to change as the working end 130 continues to move closer to the no-go area. As illustrated in FIG. 2, in most orientations the working end 130 of the instrument 16 is not substantially near or within the boundary and accordingly in most of the views the indication is low or not presented.

Figure 3:
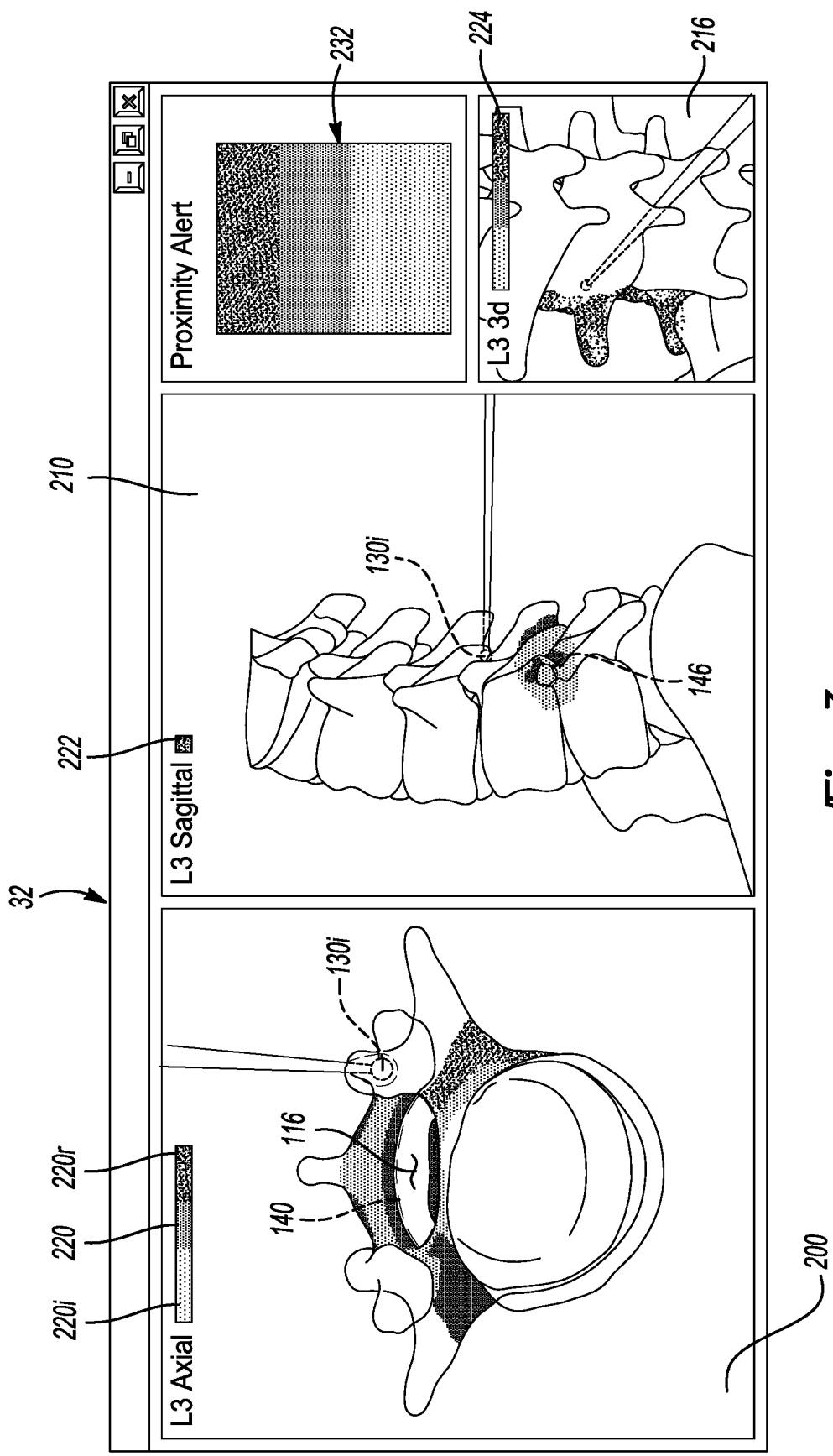
FIG. 3 is an illustration of a screen of a display device with a tracked instrument second position and indications, according to various embodiments.

Turning reference to FIG. 3, however, as the instrument 16 is moved by the user 12 and/or surgical robot the respective or various indications may also alter or change appearance to provide feedback and indication to the user 12 of a tracked position of the working end 130 relative to the no-go 146 or 140. As illustrated in FIG. 3 in the axial view, the working end icon 130i is near the vertebral foramen 116 and the predetermined no-go volume 140. Accordingly the indication 220 is increased in dimension relative to the image 30 and may also include an altered color or visual indication. In various examples, an initial portion of the indicator 220 may include a light or yellow color 220i. As the indicator 220 grows the indicator may increase in dimension and change color, such as including a gradient from yellow to red (including orange) and a red portion 220r.

The indicator 220, therefore, may provide a plurality of visual indications or audible indications to the user 12 that the working end 130 is near the predetermined no-go region 140. The overall proximity indicator 232 may also similarly change in color and dimension given the change of the indicator 220. In the sagittal view and the respective orientation presented thereby, however, the indicator 222 may not change given the relative location of the working end 130. Accordingly, in various views the working end icon 130i may at different positions relative to the predefined go or no-go areas and the respective indicators may also be different. Accordingly the 3D view 216 may also indicate or have the indicator 224 change to include the change in color, size, and/or opacity for viewing by the user 12. It is understood, however, that the user 12 may also have an assistant that is able to provide an indication, such as an auditory indication, that the visual indicators have changed. In addition the navigation system may provide additional indications to the user 12, such as auditory indications and haptic indications (e.g. haptic feedback through the instrument 16) and/or the surgical robot to the user 12.

Figure 4:
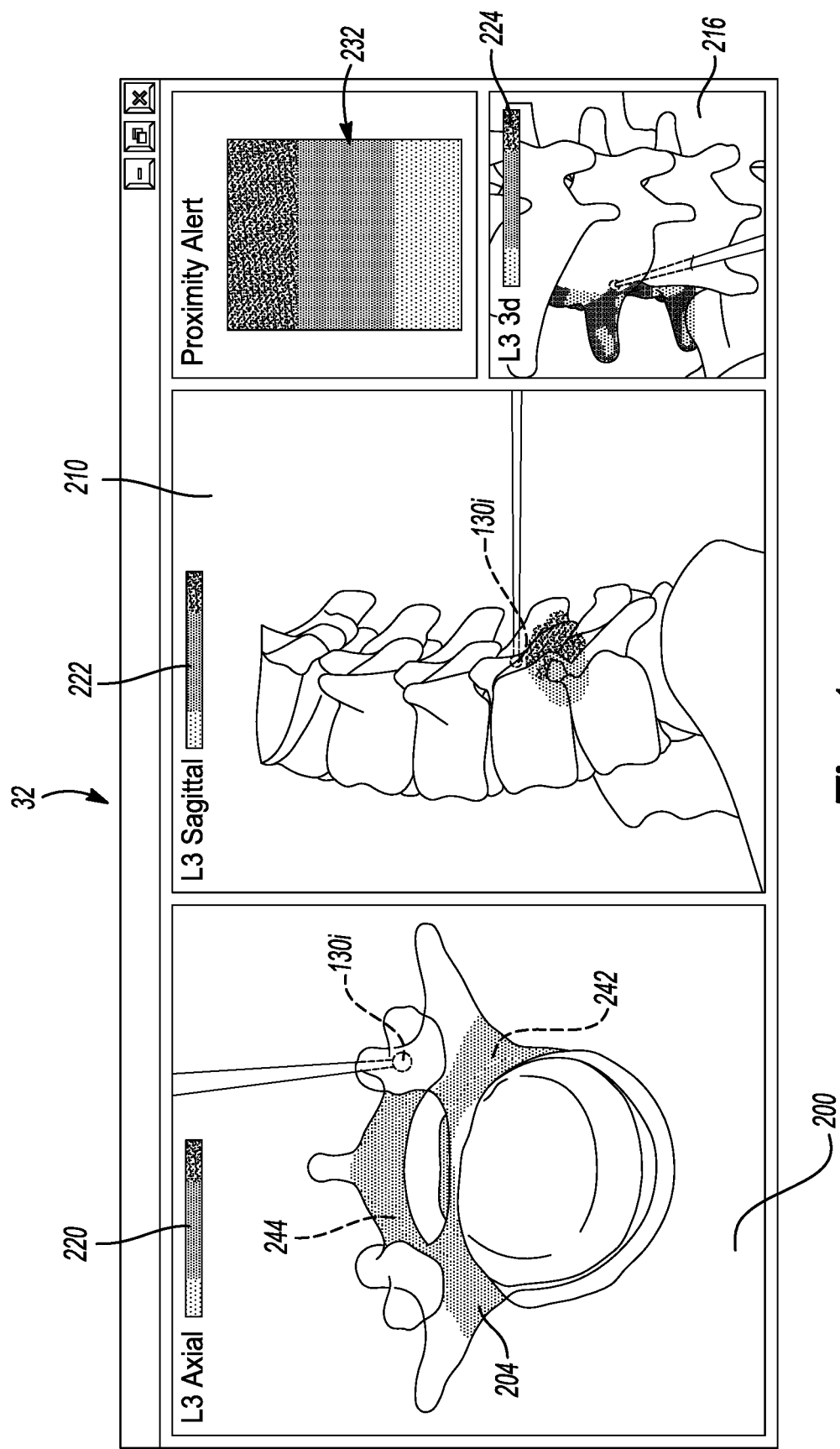
FIG. 4 is an illustration of a screen of a display device with a tracked instrument third position and indications, according to various embodiments.

Turning reference to FIG. 4, as the instrument 16 is moved the various indicators may change. For example, the indicator 220 may return or reduce in size and change color when the working end 130, represented by the icon 130i, is moved away from a selected no-go area, such as the vertebral foramen 116 volume 140. Similarly the direct image indications 240, 244, 242, may also be light (e.g. yellow) in color or indication, and/or revert to the initial non-proximity indication. However, in the sagittal view window 210, the indicator 222 may have changed to include a different size, color, or the like, as discussed above. Similarly the overall proximity indication 232 may change given the indicator 222. The three-dimensional view indicator 224 may also indicate the proximity of the working end 130 relative to the selected predefined areas or volumes. Accordingly, as the user 12 and/or surgical robot moves the instrument 16 that is tracked with the navigation system 10, the indicators on the display device 32 may change relative to the different views or view windows displayed thereon. Accordingly, the user 12 may be continuously updated, such as in substantially real time, regarding the tracked position of the instrument 12 and proximity relative to the different predefined areas.

With reference to FIG. 5, the instrument may be further moved, such as nearing an end of the procedure, such as a decompression procedure. When a procedure is nearly complete, the instrument 16 may be moved away from the vertebrae 20v. As the instrument is moved away, the various indicators 220, 222, 224, 232, in the various windows may all reduce in size and/or change color to a preliminary or initial color. Similarly the direct image indicators 240, 242, 244, may also all change or revert to an initial color, opacity, etc. It is understood that the direct image indicators 240, 242, 244, may also be provided in any appropriate view 200, 210, 216.

Accordingly, as the user 12 performs the procedure on the subject 20, for performing any appropriate procedure, such as bone removal, disc removal, soft tissue resection, etc. the various indicators, including the indicators in the selected windows and/or the direct image indicators, may alter or change to provide a visual or audible indication to the user 12 of the tracked position of the instrument relative to the predefined areas or volumes and/or the predefined distances relative to edges or boundaries thereof. Accordingly, the user 12 may view both the icons 16i and 130i representing the tracked position of the instrument 16 and working end 130, respectively, along with the additional visual indicators of the absolute tracked position of the working end 130 relative to selected predefined areas. The instrument 16 may be used to move and/or remove any selected material in a subject. The indicators may be fixed relative to the image, but may change in color, opacity, size, etc. to provide the indication to the user 12. The user 12 may, therefore, be provided substantially immediate feedback regarding the tracked position of the working end 130 of the instrument 16 relative to predefined areas or volumes of the subject 20. Thus, the procedure may be performed substantially efficiently as the user 12 is provided an indication in addition to the icon representing the instrument 16 and working in 130 on the display device 32.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system having a navigation system for performing a procedure on a subject, comprising:
    an instrument configured to interact with the subject;
    a tracking device configured to be tracked and connected to the instrument;
    a tracking system configured to track the tracking device;
    a display device configured to display at least an image of the subject;
    a processor system configured to execute instructions to:
        recall a working volume within which a working end of the instrument is selected to travel;
        recall a non-working volume within which the working end of the instrument is not to travel;
        determine the position of the working end relative to at least one of the working volume or non-working volume by tracking the tracking device with the tracking system; and
        output to the display device at least one of (i) a first indication to a user of the determined position of the working end relative to at least one of the working volume or non-working volume or (ii) a second indication to the user of the determined position of the working end relative to at least one of the working volume or non-working volume;
    wherein the first indication and the second indication are at a single indication position on the display device that changes from the first indication to the second indication;
    wherein the first indication and the second indication are both graphical representations displayed with the display device.

2. The system of claim 1, wherein the single indication position gradually changes from the first indication to the second indication.

3. The system of claim 2, wherein the first indication is a first color or first audible alert and the second indication is a second color or second audible alert.

4. The system of claim 2, wherein the first indication is a first color of a portion of the displayed image of the subject and the second indication is a second color of the portion of the subject.

5. The system of claim 1, wherein the processor system is further configured to execute instructions to:
    change the output for display with the display device from the first indication to the second indication based upon a change in the determined position of the working end relative to at least one of the working volume or non-working volume.

6. A system having a navigation system for performing a procedure on a subject, comprising:
    an instrument configured to interact with the subject;
    a tracking device configured to be tracked and connected to the instrument;
    a tracking system configured to track the tracking device;
    a display device configured to display at least an image of the subject;
    a processor system configured to execute instructions to:
        recall a working volume within which a working end of the instrument is selected to travel;
        recall a non-working volume within which the working end of the instrument is not to travel;
        determine the position of the working end relative to at least one of the working volume or non-working volume by tracking the tracking device with the tracking system; and
        output to the display device at least one of (i) a first indication to a user of the determined position of the working end relative to at least one of the working volume or non-working volume or (ii) a second indication to the user of the determined position of the working end relative to at least one of the working volume or non-working volume;
    wherein the first indication and the second indication are at a single indication position on the display device and the indication position changes from the first indication to the second indication;
    wherein the single indication position includes at least one of a horizontal bar or a vertical bar;
    wherein the second indication includes the bar of a greater length than the first indication.

* * * * *

UNITED STATES PATENT AND TRADEMARK OFFICE
CERTIFICATE OF CORRECTION

PATENT NO. : 12,004,818 B2
APPLICATION NO. : 17/338202
DATED : June 11, 2024
INVENTOR(S) : Robert J. Reddy et al.

It is certified that error appears in the above-identified patent and that said Letters Patent is hereby corrected as shown below:

On the Title Page

Page 2, Column 2, Item (56) Other Publications, Line 6, Delete "Disptach:" and insert --Dispatch:-- therefor In the Drawings Sheet 5 of 6, Fig. 4, Reference Numeral 204, Line 1, Delete "204" and insert --240-- therefor In the Specification Column 3, Detailed Description, Line 41, After "having", insert --a--

Column 5, Detailed Description, Line 4, Delete "40," and insert --42,-- therefor Column 5, Detailed Description, Line 35, Delete "72" and insert --74-- therefor Column 10, Detailed Description, Line 41, Delete "140," and insert --104,-- therefor Column 12, Detailed Description, Line 24, Delete "12" and insert --16-- therefor Signed and Sealed this
Eleventh Day of March, 2025

Coke Morgan Stewart
*Acting Director of the United States Patent and Trademark Office*